United States Patent [19]

Klatz

[11] Patent Number: 5,906,833
[45] Date of Patent: May 25, 1999

[54] CHRONOLOGICAL FOOD BAR

[76] Inventor: Ronald M. Klatz, 2434 N. Greenview Ave., Chicago, Ill. 60614

[21] Appl. No.: 08/447,224

[22] Filed: May 22, 1995

[51] Int. Cl.$^6$ ...................................................... A61K 9/26
[52] U.S. Cl. .......................... 424/468; 424/440; 424/469; 424/471; 424/94.1; 424/94.2; 426/72; 426/73; 426/74; 426/76; 428/78
[58] Field of Search .................................... 424/468, 469, 424/471, 440, 94.1, 94.2; 426/72, 73, 74, 76, 78

[56] References Cited

U.S. PATENT DOCUMENTS

| | | | |
|---|---|---|---|
| 4,752,479 | 6/1988 | Briggs et al. | 424/472 |
| 4,943,063 | 7/1990 | Moreau | 273/157 R |
| 5,227,167 | 7/1993 | Carr et al. | 424/438 |
| 5,232,709 | 8/1993 | Saltman et al. | 424/630 |
| 5,472,710 | 12/1995 | Klokkers-Bethke et al. | 424/468 |
| 5,514,382 | 5/1996 | Sultenfuss | 424/440 |
| 5,643,623 | 7/1997 | Schmitz et al. | 426/73 |

*Primary Examiner*—José G. Dees
*Assistant Examiner*—Kathryne E. Shelborne
*Attorney, Agent, or Firm*—Oliff & Berridge, PLC

[57] ABSTRACT

A nutritional supplement contains plural parts. Each of the plural parts is chronologically appropriate for its scheduled time of consumption. The nutritional supplement is contained in a palatable base, for example, a food bar which masks any unpleasant taste or texture of the nutrient. The nutritional supplement may contain any one or several nutrients including drugs, vitamins, herbs, hormones, enzymes and/or other nutrients in chronologically appropriate dosages in each part or sub-part.

25 Claims, No Drawings

CHRONOLOGICAL FOOD BAR

This invention was first disclosed to the Patent and Trademark Office in Disclosure Document No. 375118.

The present invention is generally directed to dietary supplements and nutritional food bars. More specifically, the present invention relates to scheduled delivery of a single nutrient or a mixture of nutrients in a palatable base at optimum or advantageous times with respect to the schedule of the individual consuming the dietary supplement or nutritional food bar.

BACKGROUND

Many drugs, vitamins, herbs, hormones, minerals, enzymes and other nutrients (hereinafter generally referred to as nutrients) have a very short half life in the body. A limited half life is advantageous for many nutrients because of the constantly changing conditions within a biological organism. For example, many hormones exhibit a diurnal cycle either resulting from changing metabolic activities and needs as an organism progresses through a daily cycle. For other nutrients, cycling levels are unwanted, for example, for vitamin C, a uniformly high titer is often desired.

Vitamin C is one example of a short half life nutrient. The half life of vitamin C is approximately 2 to 3 hours. Multiple dosages spaced throughout the day are essential to maintaining a desired uniformly high level of vitamin C in the body.

For other nutrients, maintaining a uniform level in a body or a tissue of an organism throughout the day is unnecessary or undesirable. For example, metabolic enhancers tend to be most effective when administered in the morning whereas other nutrients, for example, growth hormone enhancers, tend to be most effective when administered at night or before a sleep period.

Still other nutrients may require large dosages in order to be effective. For example, in order to be effective as systemic antioxidants, some vitamins would require consumption of approximately 40 tablets per day. Because of the bulk of the nutrient and/or absorptive capacity of the organism, it may be advantageous to disperse consumption of these nutrients into several doses throughout the day.

Additionally, some athletes may, as part of a multi-day training regimen, overlay a multi-day nutrient needs cycle on top of their diurnal cycle. Athletes or other competitors may also have specific chronologically determined needs, for example, an athlete may want to peak or maximize a performance during a particular scheduled event. Similarly, travelers traversing several time zones often find they must overcome their inherent diurnal cycle. A nutrient supplement satisfying their inherent or home cycle or preferably a nutrient supplement accommodating to a new cycle or helping to accommodate to a new cycle would be advantageous.

Therefore, there are several different needs for scheduling nutrient supplementation throughout the day. For some nutrients, maintenance of a uniform dosage throughout the day requires multiple scheduled administrations of nutrients throughout the day. For other nutrients, where a uniform systemic level may not be desired, scheduling timely administration of nutrients may be important. For still other supplements the physical bulk or absorptive limitations may require chronologically dispersed administrations of nutrients throughout the day. Additionally, when an individual may desire to overcome their diurnal cycle, may desire to alter their diurnal cycle or may desire to select a peak timing of their performance, a simple means for administering multiple scheduled nutritive supplements is desired.

SUMMARY OF THE INVENTION

The present invention concerns a multi-part nutritive supplement such as a food bar containing separately identifiable parts or groups of parts, each individual part or group of parts containing a chronologically appropriate dosage of drugs, vitamins, herbs, hormones, minerals, enzymes or other nutrients.

DETAILED DESCRIPTION OF PREFERRED EMBODIMENTS

The nutritive supplement of the present invention comprises a palatable base which acts as a vehicle for administering nutrients to an individual. The nutritional supplement has plural parts containing a nutrient or nutrients. Preferably, at least one of the nutrients varies in amount from one part to another. The individual parts are designed to deliver a dosage of nutrients to an organism in a chronologically appropriate manner.

Chronological appropriateness may refer to a diurnal cycle of an organism, a multi-day training regimen or ameliorating the symptoms of travel across time zones. The appropriate dosage of a nutrient or nutrients throughout a cycle, for example a diurnal cycle, may be determined by a desire to maintain a threshold value of a nutrient in an organism or a tissue of an organism. An appropriate dosage, for example, a threshold dosage, may be determined by a government entity, for example, the FDA or the USDA. A chronologically appropriate dosage is an appropriate dosage to achieve or maintain a desired level of nutrient within an organism or a portion of the organism, for example, an organ or circulatory system, appropriate for the time in the cycle for which the dosage is scheduled. Other chronologically appropriate dosages may be determined from the scientific or sports literature or other information sources or from testing the performance, for example, a treadmill test, or testing the content of nutrients or nutrient products within an individual, for example, testing the blood of an individual. A desired dosage may also be determined, for example, by an estimated consumption or utilization of a nutrient or a combination of nutrients or by a consensus of persons active or knowledgeable in, for example, an athletic or scientific discipline.

Individual parts of the nutritional supplement may vary in appropriate dosages by having a different amount of a nutrient or nutrients or by having a different formulation of nutrients.

Individual parts of the nutritional supplement may be labeled with a recommended time for consumption, such as, a target ingestion time for said portion, a countdown time to a scheduled event, symbols indicating the sequence in which they are to be taken, a pictorial representation such as a sunrise or sunset or an individual at rest or active, or other means of appropriate identification.

In an embodiment where the nutritional supplement is a food bar, the food bar can have a frangibly segmented structure. The segments can be formed by indentations, perforations or the like which serve to differentiate separate parts or subgroups of parts from one another. Alternatively, one unit of food bar can be completely divided into separate chronologically arranged sub-bars. Such sub-bars may be individually or commonly wrapped. For example, a food bar embodiment of the present invention could be shaped in the form of a Tootsie Roll™. Optionally, labels could be applied to the bar, for example in the form of a lightly adhesive strip. More preferably, labelling may be accomplished by use of edible pigments, symbols indented into the bar, shape or color coding of chronologically appropriate sub-bars or indications on a wrapper or the like.

In one preferred embodiment, the first segment or sub-bar can include a morning dosage of nutrients, e.g., drugs, vitamins, herbs, hormones, enzymes and/or other nutrients appropriate for an individual's morning dosage. A second segment or sub-bar can be dosed with the same or, preferably, a different dosage of nutrients to be chronologically appropriate for a midday dosage. A later segment can be dosed with nutrients chronologically appropriate for an evening or night time dosage. A two dosage regimen, for example, morning and night time segments, parts or sub-bars may also be appropriate. In another embodiment, hourly dosages, appropriate for the time of day, may be packaged as a daily unit or may be grouped, for example, as morning, midday, evening or night time groupings.

The substance of the bar could be, for example, a highly palatable food bar such as a dessert or candy bar, a meal bar, a nut or granola bar or other flavored, edible bar or any other consumable embodiment, for example, a chewable substance such as a Tootsie Roll™. The substance of the chronologically arranged segments or sub-bars is preferably flavored and textured to adequately mask any unpleasant taste or textures of the drugs, vitamins, herbs, hormones, enzymes and/or other nutrients to ensure palatability of the bar.

Embodiments of the present invention include but are not limited to food bars or supplements, chronologically appropriate for a diurnal cycle, a countdown to a scheduled event, for example, an athletic contest or a surgery, a cycle different from a diurnal cycle, accommodating an individual to a new diurnal cycle, and ameliorating the symptoms of stresses to an organism's diurnal cycle. The organism may be human or other animal. For example, in an embodiment involving a sporting event, the organism may be an animal, for example a racehorse. The composition of the food bar may be altered to be palatable to the organism for which it is intended.

While the invention has been described with reference to particular preferred embodiments, other embodiments and modifications can be made by those skilled in the art without departing from the spirit and scope of the invention.

What is claimed is:

1. A chronological arranged edible nutritional supplement, comprising:
   frangibly connected plural portions comprising at least a first portion and a second portion,
   said portions each being dosed with a dosage of at least one chronologically appropriate supplemental nutrient selected from the group consisting of vitamins, herbs, minerals, enzymes and drugs, at least said first portion having a different dosage from said second portion, and
   said portions each containing a dosage chronologically appropriate to achieve or maintain a desired level of said at least one nutrient within an organism or portion of the organism appropriate for the cycle that comprises a time for which the dosage is scheduled,
   wherein said chronologically appropriate supplemental nutrient is chronologically appropriate for an animal.

2. A chronologically arranged edible nutritional supplement, comprising:
   plural portions comprising at least a first portion and a second portion, said portions each being dosed with a dosage of at least one chronologically appropriate supplemental nutrient selected from the group consisting of vitamins, herbs, hormones, minerals, enzymes and drugs, at least said first portion having a different dosage from said second portion, said portions each containing a dosage chronologically appropriate for, a countdown to a scheduled event, a multi-day training regimen, resetting a diurnal cycle or ameliorating symptoms of travel across time zones,
   wherein said nutritional supplement is a food bar.

3. A nutritional supplement according to claim 2, wherein the dosages are chronologically appropriate for a countdown to a scheduled event.

4. A nutritional supplement according to claim 2, wherein the dosages are chronologically appropriate for a multi-day training regimen.

5. A nutritional supplement according to claim 2, wherein the dosages are chronologically appropriate for resetting a diurnal cycle.

6. A nutritional supplement according to claim 2, wherein the dosages are chronologically appropriate for ameliorating the symptoms of travel across time zones.

7. A nutritional supplement according to claim 1, wherein said first portion and said second portion are dosed to be chronologically appropriate for morning and night time respectively.

8. A nutritional supplement according to claim 1, wherein the plural portions further comprise a third portion.

9. A nutritional supplement according to claim 8, wherein said first, second and third portions respectively comprise a first, a second and a third dosage, said first, second and third dosages being chronologically appropriate for morning, midday and night time, respectively.

10. A nutritional supplement according to claim 1, wherein said portions are individually marked with labels identifying a chronological arrangement for said portions.

11. A nutritional supplement according to claim 10, wherein said portions are frangibly connected at peripheral indentations.

12. A nutritional supplement according to claim 10, wherein said portions are frangibly connected at peripheral perforations.

13. A chronologically arranged edible nutritional supplement, comprising:
    multiple portions comprising at least a first portion and a second portion, said portions each being dosed with a dosage of at least one chronologically appropriate supplemental nutrient selected from the group consisting of vitamins, herbs, hormones, minerals, enzymes and drugs, at least said first portion having a different dosage from said second portion, said portions each containing said at least one nutrient in a dosage chronologically appropriate to achieve or maintain a desired level of said nutrient within an organism or portion of the organism appropriate for the cycle that comprises a time for which the dosage is scheduled,
    wherein said edible nutritional supplement is a food bar, and
    wherein said first portion and said second portion are not physically connected.

14. A nutritional supplement according to claim 12, wherein said first portion and said second portion are individually wrapped.

15. A nutritional supplement according to claim 10, wherein the labels comprise at least one symbol selected from the group consisting of a color code, a pictorial representation, a word, a letter, a number, a shape, and a combination thereof.

16. A nutritional supplement according to claim 1, wherein the animal is a human.

17. A chronologically labeled edible nutritional supplement comprising a food bar having plural portions, each of said portions comprising a dosage of at least one nutrient, said dosage being appropriate to achieve a desired level of the nutrient within at least a part of an organism for a period of time, each of said portions being associated with a label indicating a target ingestion time for said portion.

18. A nutritional supplement according to claim 17, wherein a said dosage of said nutrient in one of said plural portions is different from a said dosage of said nutrient in another of said plural portions.

19. A nutritional supplement according to claim 13, wherein said portions are individually marked with a label identifying a chronological arrangement for said portions.

20. A nutritional supplement according to claim 19, wherein the label comprises at least one symbol selected from the group consisting of a color code, a pictorial representation, a word, a letter, a number, a shape, and a combination thereof.

21. A nutritional supplement according to claim 17, wherein said plural portions are frangibly connected.

22. A nutritional supplement according to claim 21, wherein said portions are frangibly connected at peripheral indentations.

23. A nutritional supplement according to claim 21, wherein said portions are frangibly connected at peripheral perforations.

24. A nutritional supplement according to claim 17, wherein said at least one nutrient is selected from the group consisting of vitamins, herbs, hormones, minerals, enzymes and drugs.

25. A nutritional supplement according to claim 17, wherein the labels comprise at least one symbol selected from the group consisting of a color code, a pictorial representation, a word, a letter, a number, a shape, and a combination thereof.

* * * * *